United States Patent [19]
Borghi

[11] Patent Number: 5,314,460
[45] Date of Patent: May 24, 1994

[54] ADAPTOR DEVICE FOR ELECTRODE CATHETERS

[76] Inventor: Enzo Borghi, Via Romagnoli, 15, 40054 Budrio, Italy

[21] Appl. No.: 840,887

[22] Filed: Feb. 25, 1992

[30] Foreign Application Priority Data

Mar. 29, 1991 [IT] Italy .............................. B091A000102

[51] Int. Cl.$^5$ ........................................... A61N 1/362
[52] U.S. Cl. .................................... 607/122; 607/115
[58] Field of Search ................................ 128/784–786, 128/419 P, 642; 607/116, 115, 119, 122, 125–128, 36–38

[56] References Cited

U.S. PATENT DOCUMENTS

| | | | |
|---|---|---|---|
| 4,411,277 | 10/1983 | Dickhudt | 128/784 |
| 4,954,105 | 9/1990 | Fischer | 128/786 |
| 5,014,720 | 5/1991 | Barcel et al. | 128/786 |
| 5,036,862 | 8/1991 | Pohndorf | 128/784 |

FOREIGN PATENT DOCUMENTS

| | | |
|---|---|---|
| 400592 | 5/1992 | European Pat. Off. . |
| 2508716 | 6/1982 | France . |

OTHER PUBLICATIONS

European Search Report Issued by EPO for Priority European Patent Application No. 92 83 0083.9 (Jul. 15, 1992).

*Primary Examiner*—William E. Kamm
*Assistant Examiner*—Jeffrey R. Jastrzab
*Attorney, Agent, or Firm*—Fay, Sharpe, Beall, Fagan, Minnich & McKee

[57] ABSTRACT

Incorporated into a pacemaker electrode, the adaptor essentially comprises an anchor element and an expander element insertable respectively into the spiral wound wires of a previously implanted electrode catheter, the ends of which are bared a suitable distance from their protective outer sleeve to facilitate the connection; the anchor element is inserted coaxially into and retained by the inner wire, while the expander element is hollow, coaxially encompassing the anchor element and affording a tapered profile that lodges stably between the outer wire and the insulating sheath of the inner wire. Use is made of a screw adjustment mechanism, associated with the end of the electrode farthest from the wires, to draw the electrode and the catheter together and seat the ends of the wires tightly in an encapsulating socket afforded by the electrode itself.

13 Claims, 2 Drawing Sheets

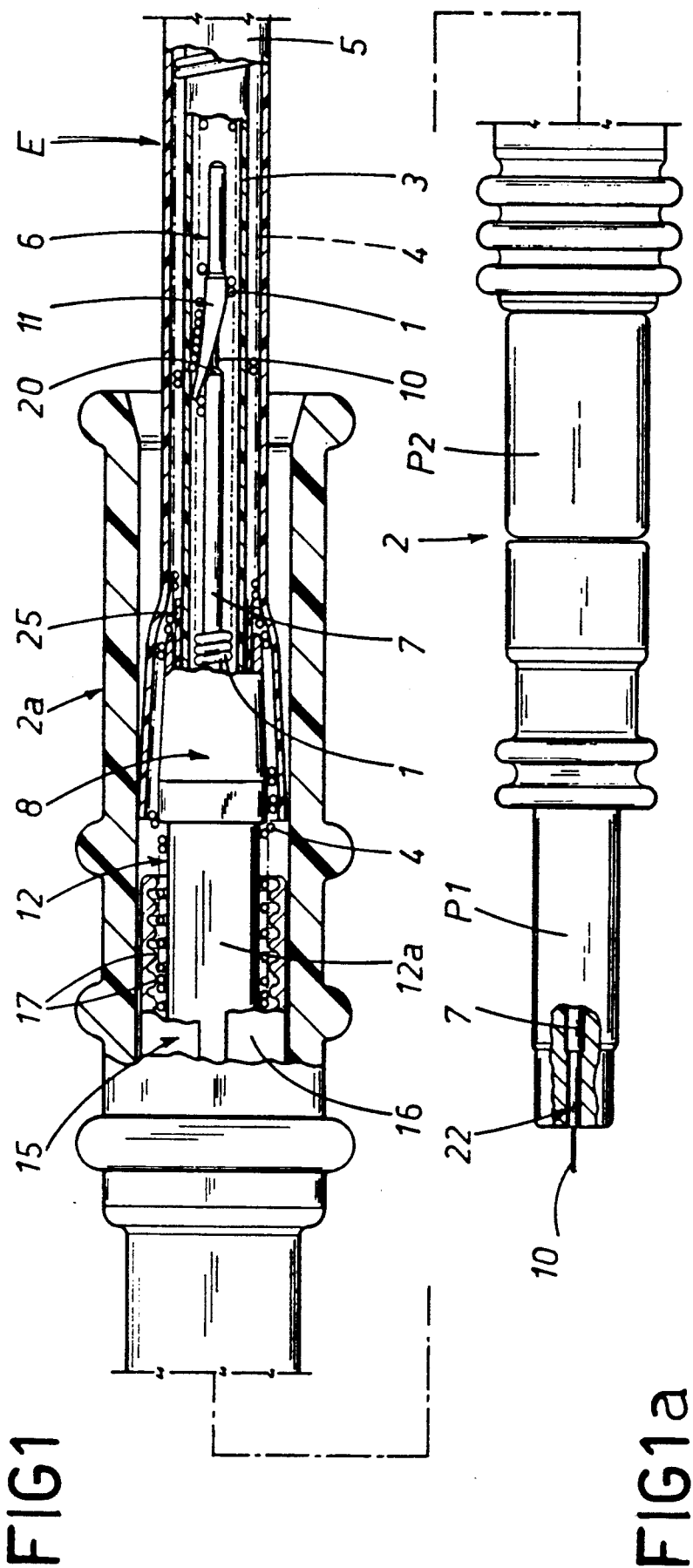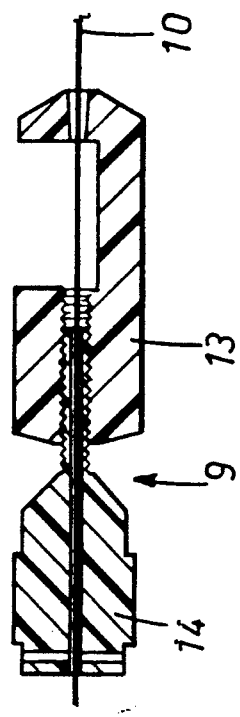
FIG1
FIG1a

ADAPTOR DEVICE FOR ELECTRODE CATHETERS

BACKGROUND of the INVENTION

The present invention relates to an adaptor device for electrode catheters, and for bipolar electrode catheters in particular.

The art field of heart surgery embraces numerous types of cardiac catheters designed for connection at one end, generally by way of a flexible tube functioning as a biocompatible outer sheath, to an artificial pacemaker implanted in the body of the patient, and carrying a terminal electrode at the remaining end which can be anchored positively to the ventricular cardiac muscle.

This particular type of catheter also incorporates a second electrode distanced and insulated from the first, positioned so as to occupy the atrium once the terminal electrode is anchored. The terminal or ventricular electrode consists generally in a sharp point affording elements such as will penetrate and thus establish a continuous and secure contact with the cardiac muscle; once implanted in this manner, the electrode is connected to a first pole of the pacemaker by way of a spiral-wound, electrically conductive wire.

It is being found currently, where patients require the replacement of an existing pacemaker rendered unreliable by reason of its low charge, irregular operation or malfunction, that problems can arise due to incompatibilities between the connectors of electrode catheters implanted in the past and those of more recent design; reflecting the ever greater technological advances being made in this field, in effect, the newer catheters are much smaller than their predecessors as the overall dimensions of the newer pacemakers also become much smaller.

Remembering that the ventricular electrode becomes embedded in time beneath a layer of organic tissue and cannot be removed (such a step is inadvisable from the medical standpoint), it happens that the solution adopted in present-day surgical practice is almost invariably one of implanting a completely new electrode catheter in the cardiac cavity for connection to the new pacemaker, and simply leaving the former electrode in place, unused, alongside the replacement.

As an alternative expedient, the prior art embraces adaptor-reducer type connectors by means of which to fashion a mechanical interface between the existing pins of a previously implanted electrode catheter and the receiver contacts of a replacement pacemaker; inevitably, this reflects a compromise from technical and medical standpoints alike as the new implant is impoverished somewhat by the large dimensions of the mechanical components utilized to effect the interface.

The object of the present invention is to overcome the problem outlined above by providing an adaptor device that can be fastened to the unattached end of a bipolar electrode catheter already in situ and used to make the requisite electrical connection to pacemakers of the latest generation; such a device will be simple in embodiment, swiftly implanted in surgery, and able to ensure a suitably dependable connection.

SUMMARY of the INVENTION

The stated object is realized in an adaptor device according to the present invention, which comprises an anchor element and an expander element by means of which to connect an electrode on the one hand, and on the other, the ends of a first and a second spiral wound wire bared from their relative sleeves and requiring connection to a pacemaker; the anchor element is insertable into and retained thus stably by the first spiral wound wire, whilst the expander element is hollow, coaxially accommodating the anchor element and embodied with a tapered profile at the end offered to the wire, in such a way as to lodge stably between the second wire and the sleeve of the first wire. The device further comprises adjustment means at the free end of the anchor element, of which the function is to draw the new electrode and the catheter together and thus seat the end of the catheter stably in the electrode.

BRIEF DESCRIPTION of the DRAWINGS

The invention will now be described in detail, by way of example, with the aid of the accompanying drawings, in which:

FIG. 1 is the side elevation of an adaptor device for cardiac electrode catheters according to the present invention, in which certain features are omitted better to reveal others;

FIG. 1a is an enlarged sectional illustration of adjustment means forming part of the device;

DESCRIPTION of the PREFERRED EMBODIMENTS

Figure 2:
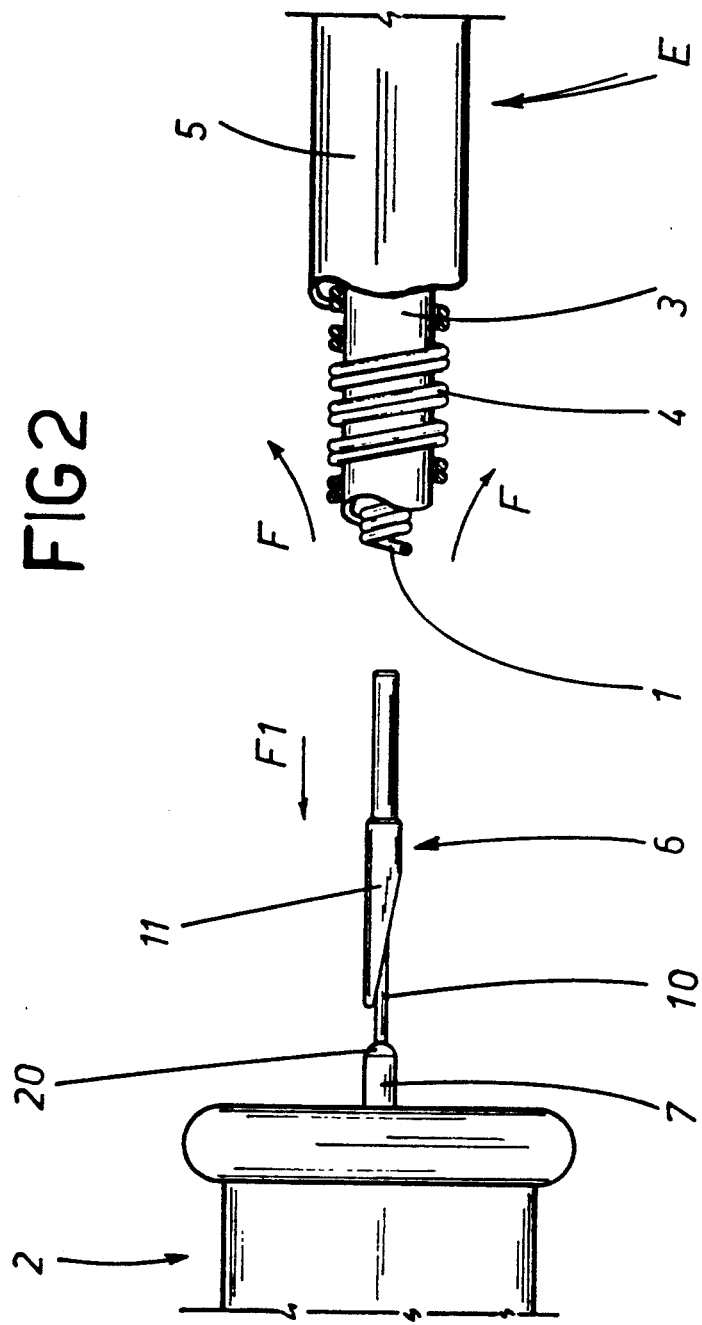
FIG. 2 is a side elevation of the device, shown before being joined to the electrode catheter and with certain parts omitted better to reveal others.

As illustrated in the drawings, an adaptor device according to the present invention is designed for use in conjunction with the electrode catheter E of a cardiac pacemaker; such a catheter is of the type comprising an internal first conductor of spiral wound wire 1 connected at one end by way of an electrode 2 (a conventional terminal electrode) to one pole P1 of a conventional cardiac pacemaker (not illustrated). The first wire 1 is ensheathed by a flexible tube 3 of insulating material, its remaining end projecting from the tube and destined to anchor positively in the ventricular wall of a cardiac muscle.

The catheter comprises a second conductor of spiral wound wire 4 coaxially encompassing the flexible tube 3, of which one end is connected to the second pole P2 of the pacemaker and the remaining end to an atrial electrode, and a protective outer sleeve denoted 5, ensheathing the second wire 4.

In an adaptor device according to the invention, which is designed for attachment to an existing electrode catheter E suitably prepared by removing the previous electrode 2 and baring the ends of the first and second spiral wound wires 1 and 4 from the outer sleeve 5, the terminal contact elements affording the two poles P1 and P2 for connection to a new cardiac pacemaker are embodied integrally with an anchor element 6 and an expander element 8 accommodated internally of a socket end portion 2a of the new electrode 2.

More exactly (see FIG. 1), the anchor element 6 is electrically conductive, coaxially insertable into and stably retainable by the first spiral wound conductor 1, and slidably associated with a rigid core 7, likewise electrically conductive, which extends coaxially through the expander element 8 and is connected at one end with the first pole P1. In effect, the anchor element 6 comprises a third wire 10 and, crimped to the end of the wire offered to the catheter E, a horizontal toggle 11 of which the projecting tip is directed back toward the electrode 2 in such a way as to remain positioned between the third wire 10 and the first wire 1. Moreover, the end of the rigid core 7 nearest the toggle 11 exhibits a rounded profile 20 formed by crimping the core 7 itself to the third wire 10, which is designed to favor an outward deflection of the toggle.

Still in FIG. 1, the end of the core 7 farthest from the toggle 11 affords a restriction 22 serving as friction means designed to interact with the third wire 10 when effecting a final adjustment (to be described more fully in due course).

The expander element 8 likewise is conductive, and of hollow embodiment, the end offered to the spiral wound wires 1 and 4 affording a tapered profile in such a way as to lodge stably between the tube 3 and the second wire 4 when the anchor element 6 is inserted. As discernible from FIG. 1, the element 8 consists in a hollow cylinder 12 of which one end affords the tapered profile and the central portion or shank 12a is accommodated stably within the electrode 2. The hollow cylinder 12 also comprises an internal second insulating sleeve 25 extending the entire length of the expander element 8 and emerging a given distance from the tapered end in such a way as to isolate the first spiral wound wire 1 from the second spiral wound wire 4.

FIG. 1a illustrates adjustment means 9 associated with the end of the anchor element 6 farthest from the toggle, which allow of drawing the catheter E toward the new electrode 2 and seating the ends of the wires tightly in the socket 2a.

In the example illustrated, such means 9 consist in a brace 13 through which the free end of the third wire 10 is inserted and secured to a jack screw 14 threadedly engaging the end of the brace 13 located farthest from the toggle 11, in such a manner that the anchor element 6 can be adjusted by jacking the screw 14 away from the brace 13, and the excess length of wire 10 then cut and discarded.

To the end of ensuring a firm association of the anchor element 6 and the expander element 8 with the respective wires 1 and 4, the electrode 2 is equipped with fastening means 15 consisting in a flexible hollow clip 16 positioned between the electrode 2 and the second spiral wound wire 4 and affording internal serrations 17 by which this same second wire 4 is pinched against the shank 12a of the expander element 8.

To enable implantation of the device in surgery, the old electrode 2 must first be removed from the catheter E and the end of the catheter then trimmed in readiness for the new connection (see FIG. 2) by baring a suitable length of the first and second wires 1 and 4 from the outer sleeve 5; in addition, the free end of the second wire 4 is splayed to a certain degree using a cone point tool (see arrows denoted F in FIG. 2) in order to favor a suitably deep insertion of the expander element 8.

At this juncture, the socket end 2a of the new electrode 2, containing the adaptor device, can be offered to the prepared end of the catheter E in such a way that the toggle 11 and the third wire 10 are inserted coaxially into the bore of the first wire 1, and an initial contact is brought about between the tapered end of the expander element 8 and the second wire 4, whereupon a rotary movement is applied to carry the wire 4 over the expander element 8 and into contact with the back of the socket 2a. Thereafter, the surgeon utilizes the brace 13 and the jack screw 14 to draw the third wire 10 into the electrode 2 (arrow F1, FIG. 2), thereby wedging the toggle 11 between the third wire and the first wire 1 (a movement favored also by the rounded end of the rigid core 7). This same step has the effect of seating the relative end of the catheter E firmly in the new electrode 2, which is then closed permanently, e.g. by stitching the rim of the socket 2a, in such a way that no space remains between the rim and the outer sleeve 5. This done, it remains only to cut away the part of the third wire 10 still attached to the brace 13 and issuing from the electrode 2, and to secure the connection between the spiral wound wires and the relative parts in contact by tightening the clip 16 over the second wire 4 (likewise, stitching around the parts in question).

Thus, with a device according to the invention, it becomes possible to keep a previously implanted electrode catheter in use even when implanting a new pacemaker, without causing undue disturbance to the patient; the operation of replacing the old electrode is swift and precise, whilst the anchor and expander elements ensure there is no break in continuity of atrial signals between the pacemaker and the patient's heart.

What is claimed is:

1. An apparatus comprising a conductive catheter comprising:

an internal, first electrically conductive spiral wound wire ensheathed by an electrically insulating flexible tube, of which a first end is adapted to be connected by way of an electrode to a first pole of a pacemaker and a remaining end terminates in an element adapted to be secured positively to a ventricular wall of a cardiac muscle;

a second electrically conductive spiral wound wire, coaxially ensheathing the flexible tube and ensheathed in turn by a first protective outer sleeve, of which a first end is adapted to be connected to a second pole of the pacemaker and a remaining end is adapted to be connected to an atrial electrode;

a single bipolar electrode with a socket end portion and poles comprising two terminal contact elements for enabling connection to a pacemaker implanted in conjunction with an existing catheter from which a previous electrode has been removed and of which said first and second wires are bared a suitable distance from the first protective outer sleeve;

an electrically conductive hollow expander element coaxially and stably accommodated within the socket end portion of the electrode and associated with the second pole of which at least a free end is of tapered profile and insertable stably between the flexible tube and the second spiral wound wire;

a rigid core associated at one end with a first pole of the electrode and at the remaining end with an electrically conductive anchor element that is positioned internally of and coaxial with the expander element, and an anchor element capable of sliding movement coaxially with and in relation to the socket end portion and insertable into and stably retainable by the first spiral wound wire;

adjustment means associated at least with the free end of the electrode for selectively producing sliding movement of the anchor element to cause the electrode and the catheter to be drawn together for seating the catheter in the socket end portion.

2. A device as in claim 1, wherein the rigid core is embodied with a rounded profile at an end nearest the catheter, and occupies a stable position internally of the electrode, whilst the anchor element consists of a third wire slidably accommodated within the core, and a horizontal toggle secured to a first end of the third wire nearest the catheter, of which a projecting tip is directed back into the electrode in such a way that when the electrode and catheter are drawn together, the third wire slides through the core and the horizontal toggle is caused to lodge stably between the third wire and the first spiral wound wire, the projecting tip being deflected by the rounded profile of the core.

3. A device as in claim 1, wherein the socket end portion incorporates a fastener, to a rear of the expander element, consisting of a hollow flexible clip positioned between the socket end portion and the second spiral wound wire and affording internal serrations by which the second wire is pinched against the expander element.

4. A device as in claim 1, wherein the expander element consists of a hollow cylinder comprising a central shank rigidly associated with the electrode and affording an internal second insulating sleeve extending the entire length of the expander element and emerging a given distance from the tapered free end.

5. A device as in claim 1, wherein the adjustment means consists of a brace through which a free end of a third wire is inserted and secured to a jack screw threadedly engaging an end of the brace located farthest from the toggle, in such a manner that the anchor element can be adjusted by jacking the screw away from the brace and then trimmed.

6. An apparatus for enabling electrical connection to a pacemaker having first and second poles comprising:
   a conductive catheter having first and second spiral wound wires, the spiral wound wires being separated by a flexible insulating wall;
   a conductive expander means for establishing electrical connection between the second pole of the pacemaker and the second spiral wound wire, the conductive expander means having a first end adapted to be inserted between the second spiral wound wire and the flexible insulating wall and a second end adapted to be connected to the second pole of the pacemaker;
   a conductive core means for establishing electrical connection between the first pole of the pacemaker and the first spiral wound wire, the conductive core means being associated with the conductive expander means and having a first end adapted to be inserted into the first spiral wound wire and a second end adapted to be connected to the first pole of the pacemaker;
   a conductive anchor means for securing connection of the apparatus to the pacemaker, having a first end contained within the conductive core means and a second end adapted to be inserted into the first spiral wound wire.

7. The apparatus of claim 6 wherein the first spiral wound wire is positioned concentrically within the second spiral wound wire.

8. The apparatus of claim 7 wherein the flexible insulating wall is formedly a flexible insulating tube positioned concentrically between the first and second spiral wound wires.

9. The apparatus of claim 8 wherein the conductive core means is positioned concentrically within the conductive expander means.

10. The apparatus according to claim 6 further comprising an adjustment means connected to the first end of the conductive anchor means for adjusting the anchor means position within the first spiral wound wire.

11. The apparatus according to claim 6 wherein the anchor means further comprises a wire having a first end, a second end and a toggle fixedly attached to the second end of the anchor means wire.

12. The apparatus of claim 6 wherein the first end of the conductive core means is crimped.

13. The apparatus of claim 6 wherein the first end of the conductive expander means is tapered.

* * * * *